United States Patent
Pai

(10) Patent No.: US 11,116,941 B2
(45) Date of Patent: Sep. 14, 2021

(54) CATHETER CURVE SHAPE STRUT

(71) Applicant: St. Jude Medical, Atrial Fibrillation Division, Inc., St. Paul, MN (US)

(72) Inventor: Sameer Pai, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 526 days.

(21) Appl. No.: 15/103,723

(22) PCT Filed: Nov. 20, 2014

(86) PCT No.: PCT/US2014/066579
§ 371 (c)(1),
(2) Date: Jun. 10, 2016

(87) PCT Pub. No.: WO2015/088733
PCT Pub. Date: Jun. 18, 2015

(65) Prior Publication Data
US 2016/0310701 A1    Oct. 27, 2016

Related U.S. Application Data

(60) Provisional application No. 61/914,346, filed on Dec. 10, 2013.

(51) Int. Cl.
*A61B 18/14* (2006.01)
*A61M 25/01* (2006.01)
(Continued)

(52) U.S. Cl.
CPC ....... *A61M 25/0138* (2013.01); *A61B 1/0055* (2013.01); *A61B 18/1492* (2013.01);
(Continued)

(58) Field of Classification Search
CPC ... A61B 2017/003–00309; A61B 2017/00305; A61B 18/1492; A61B 18/1467
See application file for complete search history.

(56) References Cited

U.S. PATENT DOCUMENTS

| 4,580,551 A | 4/1986 | Siegmund et al. |
| 5,322,064 A | 6/1994 | Lundquist |
| (Continued) | | |

FOREIGN PATENT DOCUMENTS

| EP | 2301617 A1 | 3/2011 |
| EP | 2666426 A1 | 11/2013 |
| (Continued) | | |

*Primary Examiner* — Jaymi E Della
(74) *Attorney, Agent, or Firm* — Dykema Gossett PLLC

(57) ABSTRACT

Catheter curve shape struts for steerable medical devices such as catheters are disclosed. These struts may not only help shape a steerable portion of a medical device (e.g., a distal portion of a catheter), but also may help to return a steered or deflected portion of the medical device to an uncurved configuration when it is no longer desirable or necessary to steer or deflect the medical device. These struts may include first and second pluralities of complementary, staggered cutout regions. When used in a catheter that is deployed via an introducer, at least some configurations of the catheter curve shape strut can enable the catheter to be rotated about its longitudinal axis, even when the distal deflectable section is in a curved configuration and inside of the introducer.

23 Claims, 20 Drawing Sheets

(51) Int. Cl.
*A61B 1/005* (2006.01)
*A61B 18/00* (2006.01)

(52) U.S. Cl.
CPC ............ *A61M 25/0147* (2013.01); *A61B 2018/00577* (2013.01); *A61B 2218/002* (2013.01); *A61M 2205/0266* (2013.01)

(56) References Cited

U.S. PATENT DOCUMENTS

| | | | |
|---|---|---|---|
| 5,329,923 A * | 7/1994 | Lundquist | A61B 18/1492 600/373 |
| 5,507,751 A * | 4/1996 | Goode | A61B 17/221 604/264 |
| 5,817,015 A * | 10/1998 | Adair | A61B 1/00101 600/121 |
| 5,911,715 A | 6/1999 | Berg et al. | |
| 6,300,875 B1 | 10/2001 | Makower et al. | |
| 6,493,590 B1 | 12/2002 | Wessman et al. | |
| 6,585,718 B2 | 7/2003 | Hayzelden et al. | |
| 6,749,560 B1 | 6/2004 | Konstorum et al. | |
| 8,376,991 B2 | 2/2013 | Kauphusman et al. | |
| 8,444,637 B2 | 5/2013 | Podmore et al. | |
| 8,475,449 B2 | 7/2013 | Werneth et al. | |
| 8,500,733 B2 | 8/2013 | Watson | |
| 2001/0037084 A1 | 11/2001 | Nardeo | |
| 2005/0033265 A1* | 2/2005 | Engel | A61B 17/3421 604/523 |
| 2005/0177132 A1* | 8/2005 | Lentz | A61M 25/0013 604/525 |
| 2005/0267444 A1 | 12/2005 | Griffin et al. | |
| 2006/0095074 A1* | 5/2006 | Lee | A61B 17/29 606/205 |
| 2008/0097393 A1* | 4/2008 | Chen | A61M 25/09 604/523 |
| 2010/0168717 A1 | 7/2010 | Grasse et al. | |
| 2010/0286626 A1 | 11/2010 | Petersen et al. | |
| 2010/0331776 A1 | 12/2010 | Salahieh et al. | |
| 2011/0160680 A1 | 6/2011 | Cage et al. | |
| 2013/0116705 A1 | 5/2013 | Salahieh et al. | |
| 2013/0296780 A1 | 11/2013 | Tegg | |
| 2013/0304034 A1 | 11/2013 | Cabiri | |

FOREIGN PATENT DOCUMENTS

| | | | | |
|---|---|---|---|---|
| JP | H07-255855 A | 10/1995 | | |
| JP | H10-501162 A | 2/1998 | | |
| JP | 2012-518470 A | 8/2012 | | |
| JP | 2012-213478 A | 11/2012 | | |
| WO | 199320877 A1 | 10/1993 | | |
| WO | 199533513 A1 | 12/1995 | | |
| WO | 2010096347 A1 | 8/2010 | | |
| WO | 2012020521 A1 | 2/2012 | | |
| WO | WO2015-125334 * | 8/2015 | ........ A61B 1/0055 |

* cited by examiner

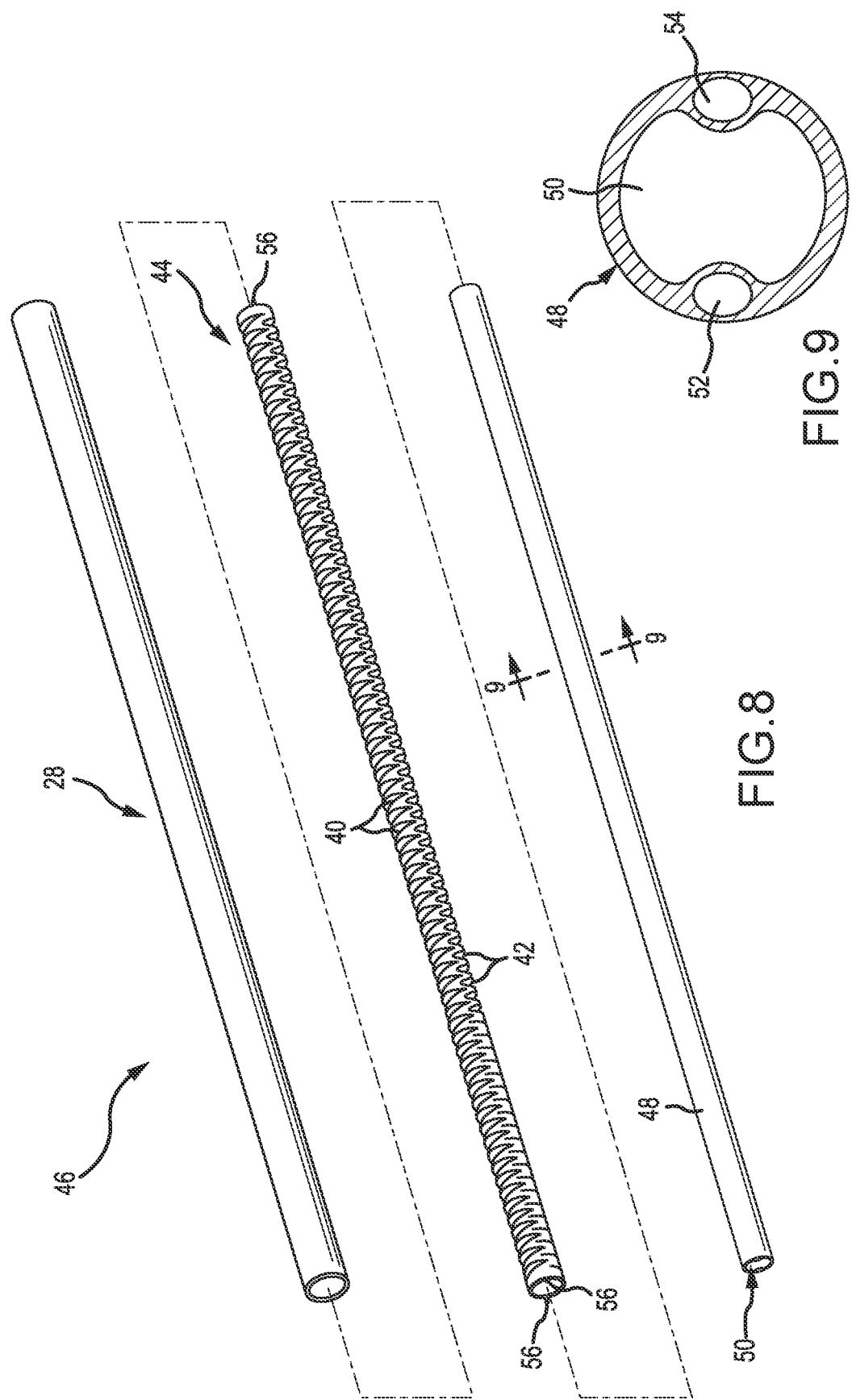

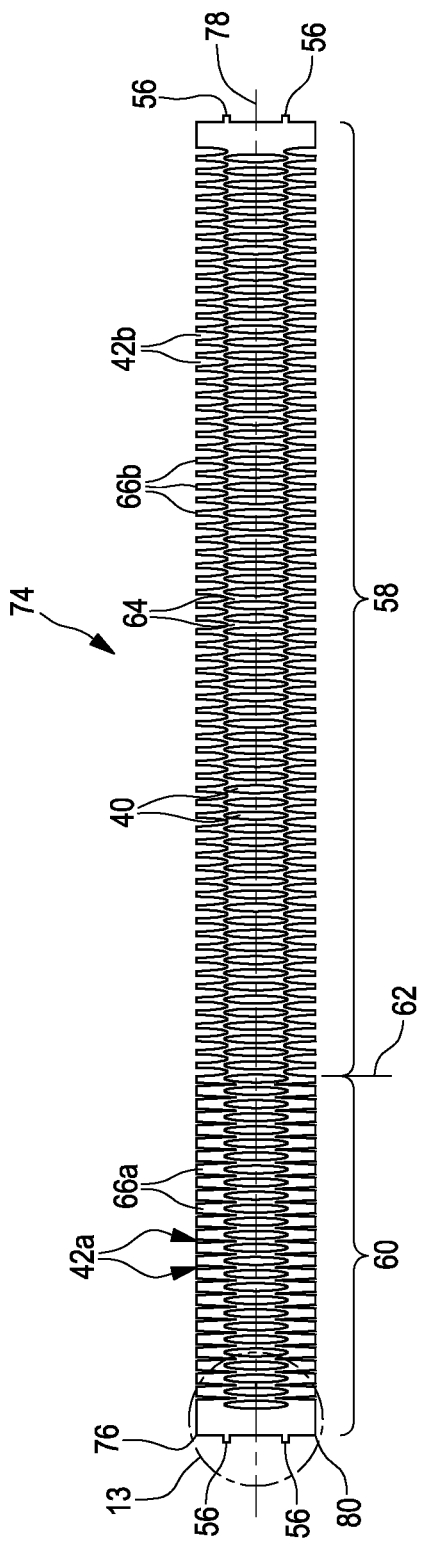
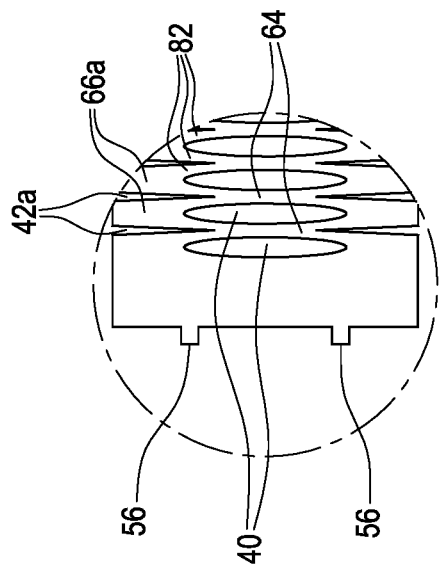

CATHETER CURVE SHAPE STRUT

BACKGROUND a. Field

The instant disclosure relates to components for steerable medical devices. In one particular form, the disclosure relates to a strut comprising part of a distal deflectable section of an electrophysiology catheter to facilitate predictable and repeatable asymmetric and symmetric deflection of the distal deflectable section.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. In some procedures, the catheter imparts ablative energy to cardiac tissue to create one or more lesions in the cardiac tissue. These lesions disrupt undesirable cardiac activation pathways and thereby limit, corral, or otherwise prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire or other tension member attached or anchored at the distal end of the catheter and extending proximally to an actuator in a control handle that controls the application of tension on the pull wire.

The foregoing discussion is intended only to illustrate the present field and should not be taken as a disavowal of claim scope.

BRIEF SUMMARY

It is desirable to be able to ensure that a deflectable portion of a catheter shaft may be predictably deflected in a preferentially-planer manner whenever desired throughout a medical procedure. It is also desirable to be able to tailor total deflectability of the catheter distal portion and the curve shape of the deflectable portion throughout the full deflection of the catheter shaft.

In one embodiment, a catheter curve shape strut comprises a longitudinally-extending cylindrical wall, the wall having an outer surface, an outer surface circumference, and an outer surface length measured longitudinally. The wall comprises connected end-to-end cylindrical sections including at least a first cylindrical section and a second cylindrical section. There are a plurality of first slots through the cylindrical wall and sequentially arranged along a first line extending longitudinally along the wall outer surface in both the first cylindrical section and the second cylindrical section. There are a plurality of second slots through the cylindrical wall and sequentially arranged along a second line extending longitudinally along the wall outer surface in both the first cylindrical section and the second cylindrical section. The slots in the plurality of second slots are longitudinally offset from the slots in the plurality of first slot. Also, the plurality of second slots further comprises second slots of a first type and second slots of a second type. The second slots of the first type are sequentially arranged along the second line only along the first cylindrical section, and the second slots of the second type are sequentially arranged along the second line only along the second cylindrical section. In some embodiments, the second slots of the second type are longer in a circumferential dimension than one-half of the outer surface circumference, whereby at least some of the second slots of the second type circumferentially overlap with at least some of the slots in the first plurality of slots. An expansion gap may be present between at least some of the end-to-end cylindrical sections.

In another embodiment, a catheter curve shape strut is configured to facilitate preferentially-planar, asymmetric deflection of a medical device. The catheter curve shape strut comprises the following: (1) a longitudinally-extending cylindrical wall, the wall having an outer surface, an outer surface circumference, and an outer surface length measured longitudinally, wherein a first line extends longitudinally along the outer surface, wherein a second line extends longitudinally along the outer surface, and wherein the second line is circumferentially offset from the first line by 180 degrees; (2) a plurality of first slots through the cylindrical wall and sequentially present along the first line, wherein each first slot has a first slot length measured circumferentially on the outer surface between first slot ends, wherein each first slot has a first slot width measured longitudinally on the outer surface, and wherein the first slot length is greater than the first slot width; (3) a plurality of first arches, wherein each first arch is present between a pair of longitudinally-adjacent first slots, wherein each first arch has a first arch length measured circumferentially on the outer surface, wherein each first arch has a first arch width measured longitudinally on the outer surface, and wherein the first arch length is greater than the first arch width; (4) a plurality of second slots through the cylindrical wall and sequentially present along the second line, wherein each second slot has a second slot length measured circumferentially on the outer surface between second slot ends, wherein each second slot has a second slot width measured longitudinally on the outer surface, and wherein the second slot length is greater than the second slot width; and; (5) a plurality of second arches, wherein each second arch is present between a pair of longitudinally-adjacent second slots, wherein each second arch has a second arch length measured circumferentially on the outer surface, wherein each second arch has a second arch width measured longitudinally on the outer surface, and wherein the second arch length is greater than the second arch width, wherein at least one of the first slot length and the second slot length is greater than one-half of the outer surface circumference. The catheter curve shape strut may further comprise a plurality of bridges connecting the first arches to the second arches. The plurality of bridges may define first and second diametrically-opposed serpentine backbones. The catheter curve shape strut may further comprise at least two alignment tabs on each longitudinal end of the strut.

In yet another embodiment, a catheter curve shape strut assembly comprises a curve shape strut, an outer body surrounding the curve shape strut, and an insert component surrounded by the curve shape strut. The outer body may comprise a single polymer layer. The insert component may be formed from an extruded polymer and may comprise three longitudinally-extending lumens, including a central lumen straddled by a pair of pull wire lumens that may be diametrically-opposed.

In another embodiment, a distal deflectable portion of an ablation catheter comprises a catheter curve shape strut assembly, a tip electrode affixed to the distal end of the catheter curve shape strut assembly, a plurality of ring electrodes affixed to the catheter curve shape strut assembly proximal to the tip electrode, a pull ring affixed to the catheter curve shape strut assembly proximal to the plurality of ring electrodes, a coupler affixed to the proximal end of the catheter curve shape strut assembly, and first and second pull wires, each pull wire having a distal end affixed to the pull ring. The first pull wire may extend proximally from the pull ring through the first pull wire management channel, and the second pull wire may extend proximally from the pull ring through the second pull wire management channel.

In a further embodiment, a catheter comprises an elongated catheter shaft comprising a distal deflectable section, first and second pull wires (each pull wire having a proximal end and a distal end) extending along the elongated catheter shaft, an actuator operatively coupled to the proximal ends of the first and second pull wires and adapted selectively deflect the distal deflectable section, a curve shape strut assembly comprising part of the distal deflectable section and itself comprising a curve shape strut mounted within an outer jacket, and a pull ring affixed to the distal ends of the first and second pull wires.

The foregoing and other aspects, features, details, utilities, and advantages of the present disclosure will be apparent by reading the following description and claims, and from reviewing the accompanying drawings.

BRIEF DESCRIPTION OF THE DRAWINGS

FIG. 8 is an exploded, isometric, assembly view of the strut assembly depicted in FIGS. 5-7, revealing details about the components of the strut assembly.

FIG. 9 is a cross-sectional view of the insert component, taken along line 9-9 of FIG. 8.

FIG. 12 is a planar view of a flat, two-dimensional cut pattern that could be used to automate the production of the strut depicted in, for example, FIG. 10.

FIG. 13 is an enlarged view of the circled portion of FIG. 12.

DETAILED DESCRIPTION

Figure 1:
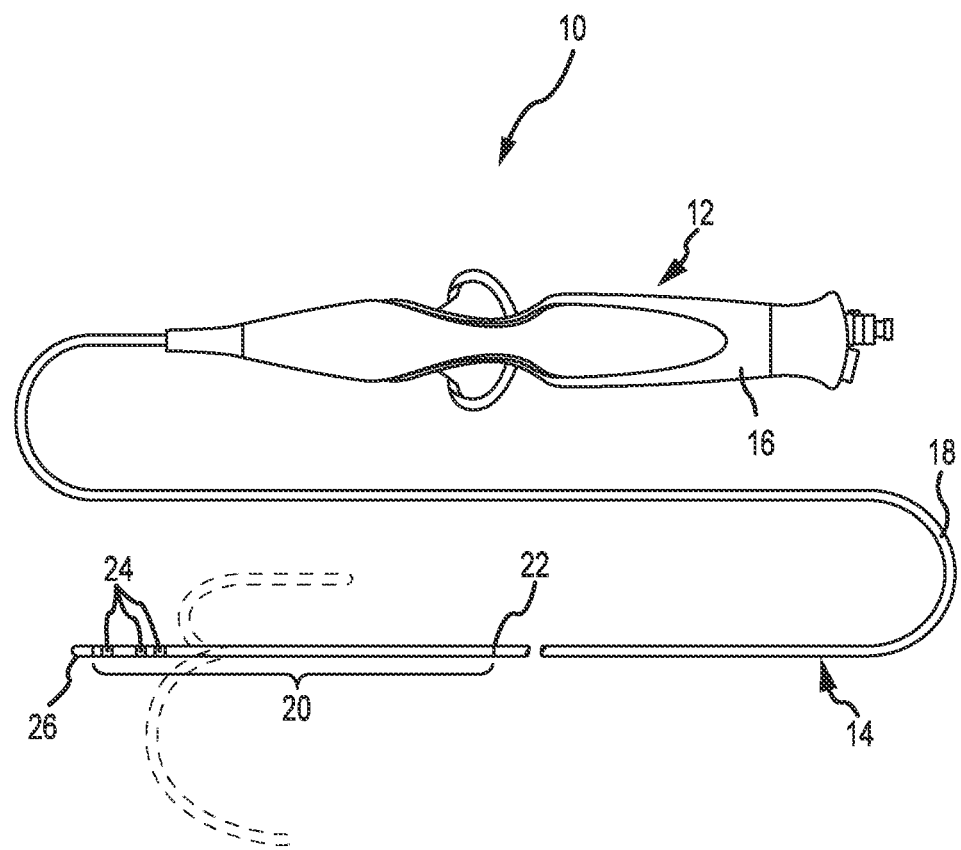
FIG. 1 depicts a representative ablation catheter having a distal deflectable section configured to create asymmetric curve shapes when deflected in different directions, as represented by the two curves shown in phantom.

FIG. 1 depicts a representative catheter 10 compromising a catheter curve shape strut (not directly visible in FIG. 1). In particular, this catheter includes a handle 12 and a catheter shaft 14. The handle 12 comprises a housing 16 that houses an actuator (not shown). The catheter shaft comprises a proximal section 18 and a distal deflectable section 20 connected at a juncture 22. As shown in FIG. 1, the distal deflectable section 20 is mounted to the distal end of the proximal catheter shaft and includes, in this embodiment, three ring electrodes 24 and a tip electrode 26. As shown in phantom in FIG. 1, the catheter curve shaped strut comprising part of the distal deflectable section 20 facilitates the formation of asymmetric curves upon deflection of the distal section in different directions. Although the phantom lines in this figure schematically depict the curves commencing from the same longitudinal position along the catheter shaft, the curves could each commence at a different longitudinal location along the catheter shaft. Also, and as discussed further below, although FIG. 1 depicts asymmetric curves, the distal deflectable section could be constructed to deflect symmetrically.

Figure 2:
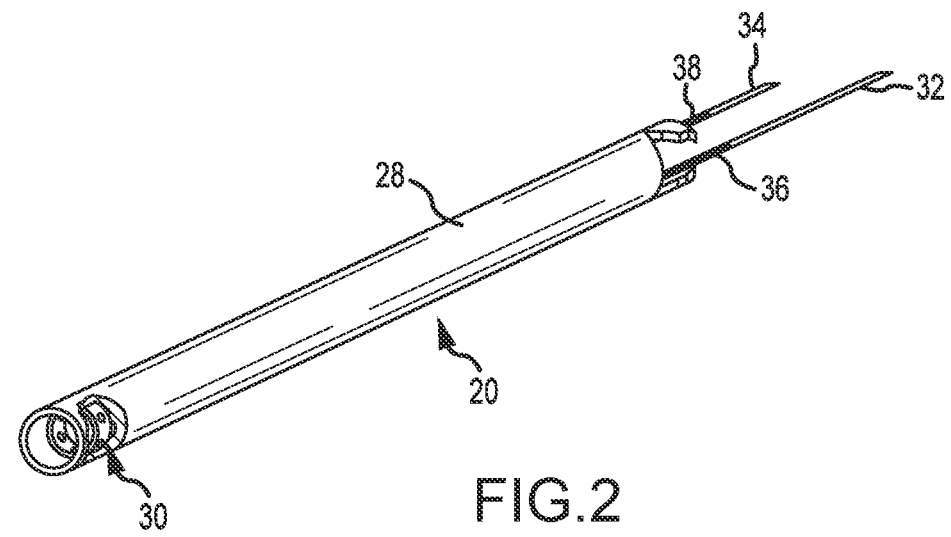
FIG. 2 is a fragmentary, isometric view of a portion of the distal deflectable section, with sections on each end broken away to reveal various details.

FIG. 2 is a fragmentary, isometric view of a portion of the distal deflectable section depicted in FIG. 1. In FIG. 2, however, the ring electrodes and tip electrode have been removed, and the distal deflectable section 20 has been separated from the proximal catheter shaft 18. In this figure, a portion of the outer body (or outer jacket or outer layer) 28 of the distal deflectable section has been broken away on the distal end (i.e., the left-hand end as oriented in FIG. 2) of the distal deflectable section to reveal a representative pull ring 30. Similarly, at the proximal end (i.e., the right-hand end as oriented in FIG. 2) of the distal deflectable section 20, another fragment of the outer body has been broken away to reveal first and second pull wires 32, 34, respectively, entering the proximal end of the distal deflectable section on their way to the pull ring. As shown in FIG. 2, first and second tightly-wound compression coils 36, 38 may surround the first and second pull wires 32, 34, respectively. Although these compression coils are shown in FIG. 2 to terminate just proximal to the proximal end of the distal deflectable section, these tightly-wound compression coils, in reality, may extend through the entire length of the proximal catheter shaft 18 to the handle 12.

Figure 3:
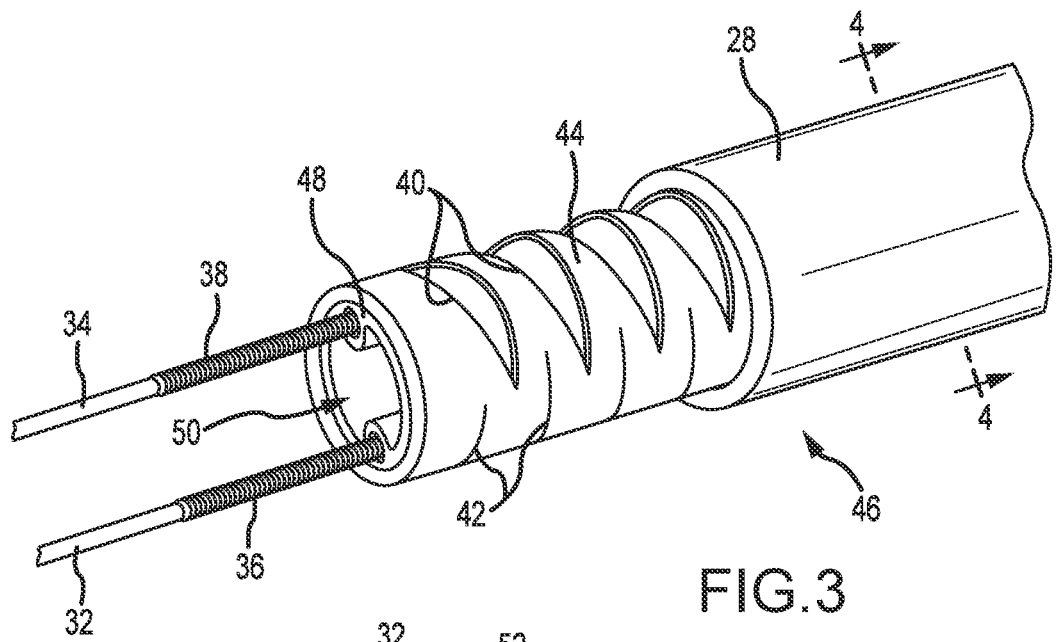
FIG. 3 is a fragmentary, isometric view of the proximal end of a strut assembly and pull wires, with a portion of an outer body of the strut assembly removed to show various features of a strut and of an insert component comprising part of the strut assembly.
Figure 4:
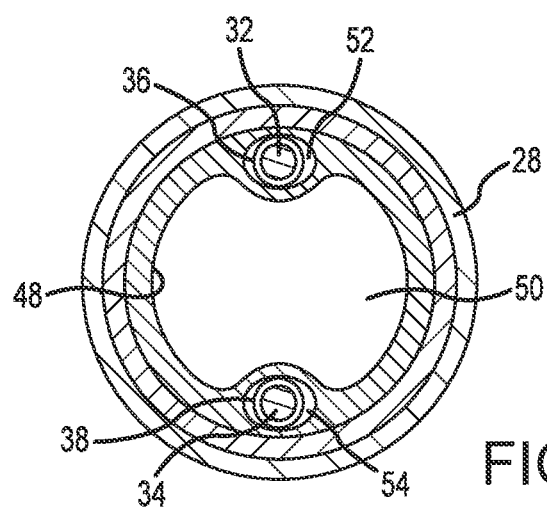
FIG. 4 is a cross-sectional view taken along line 4-4 of FIG. 3.
Figure 5:
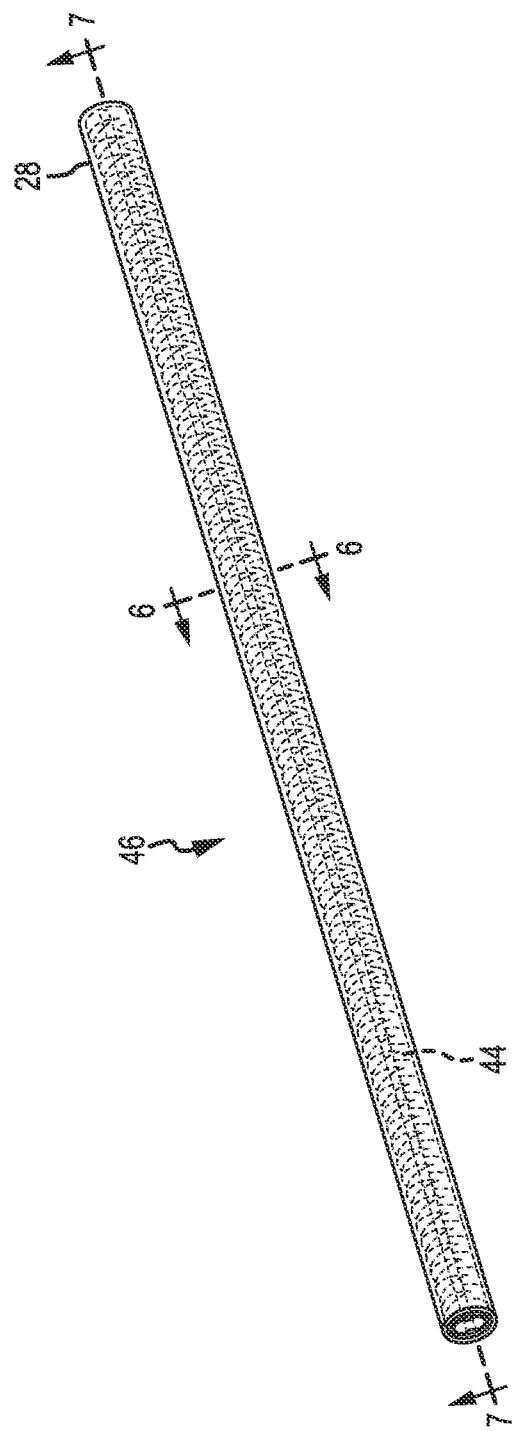
FIG. 5 is an isometric view of a strut assembly, depicted with a strut shown in phantom within the outer body of the strut assembly, and with the pull wires removed.

FIG. 3 is an enlarged, fragmentary, isometric view of the proximal end of the distal deflectable section, shown with a portion of the outer body 28 removed to reveal a plurality of cutout regions (or slots or channels or gaps), including a first plurality of cutout regions 40 and a second plurality of cutout regions 42, formed in the strut 44 comprising part of the strut assembly (see element 46 in FIG. 5). As shown in FIG. 3, the strut assembly includes the outer jacket 28, the strut 44, and an insert component 48, which may be, for example, made from an extruded polymer. The strut may be constructed from a super-elastic Nitinol and, in one embodiment, the outer body comprises a single layer of polymer material. The outer body 28 could, however, comprise multiple layers, including layers of different types of materials. As clearly shown in FIG. 3, the insert component 48 may comprise a section of tri-lumen tubing, including a single central lumen 50 that is straddled by a pair of diametrically-opposed pull wire lumens 52, 54 (see, e.g., FIG. 4). As discussed further below, these pull wire lumens must be properly oriented relative to a cut pattern (various representative cut patterns are depicted in FIGS. 12-14 and FIGS. 18-20) in the strut for the distal deflectable section to deflect as desired. FIG. 4 is a cross-sectional view of the strut assembly 46 depicted in FIG. 3, taken along line 4-4 of FIG. 3. As clearly shown in FIG. 4, the insert component 48 includes a large central lumen 50 for wire management, for example, and the two offset pull wire lumens 52, 54 (shown as diametrically opposed from each other in this embodiment).

Figure 6:
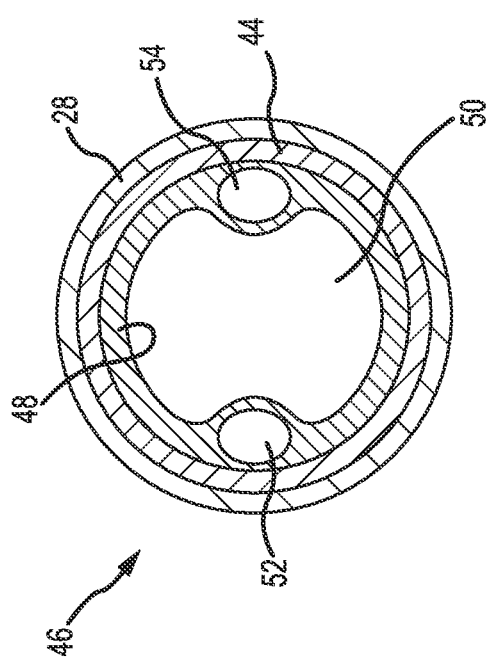
FIG. 6 is a cross-sectional view of the strut assembly depicted in FIG. 5, taken along line 6-6 of FIG. 5.
Figure 7:
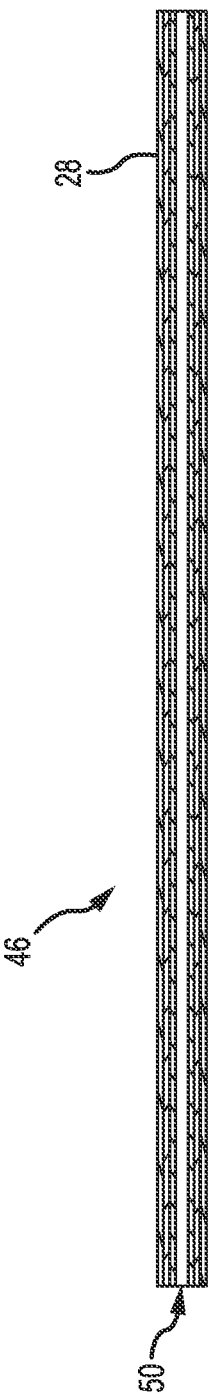
FIG. 7 is a cross-sectional view of the strut assembly depicted in FIG. 5, taken along line 7-7 of FIG. 5.

FIG. 5 is an isometric view of a strut assembly 46. In this figure, the strut 44 comprising part of the strut assembly is depicted in phantom below the outer body. FIG. 6 is a lateral cross-sectional view of the strut assembly, taken along line 6-6 of FIG. 5. FIG. 7 is a longitudinal cross-sectional view of the strut assembly depicted in FIG. 5, taken along line 7-7 of FIG. 5.

FIG. 8 shows the components of the strut assembly 46 depicted in FIGS. 5-7 prior to assembly and a reflow process. As represented by the staggered, serpentine dashed lines in FIG. 8, the strut assembly 46 is constructed by placing the insert component 48 into the strut 44, and then inserting the combined strut and insert component into the outer body 28. That assembly of the insert component, the strut, and the outer body would then be subjected to a reflow process to help lock the components together into a functional strut assembly. Also clearly visible for the first time in FIG. 8 are alignment tabs (or pin) 56 on the longitudinal ends of the strut. Although the strut embodiment shown in FIG. 8 has two alignment tabs on each of its longitudinal ends (note that only one of the two alignment tabs on the right-hand end of the strut as oriented in FIG. 8 is visible), any number of alignment tabs could be used. Two alignment tabs per end, each tab being approximately 0.01 inches by 0.01 inches, has been found to work well. As explained further below, the alignment tabs help ensure that the pull wires ultimately end up correctly oriented relative to the cutout pattern in the strut, so as to be able to effectuate deflection of the distal deflectable section. The alignment tabs also facilitate torque transfer along the catheter shaft. FIG. 9 is a cross-sectional view taken along 9-9 of FIG. 8, and clearly depicts the diametrically-opposed pull wire lumen (or channels) 52, 54 and the large central wire management lumen 50.

Figure 10:
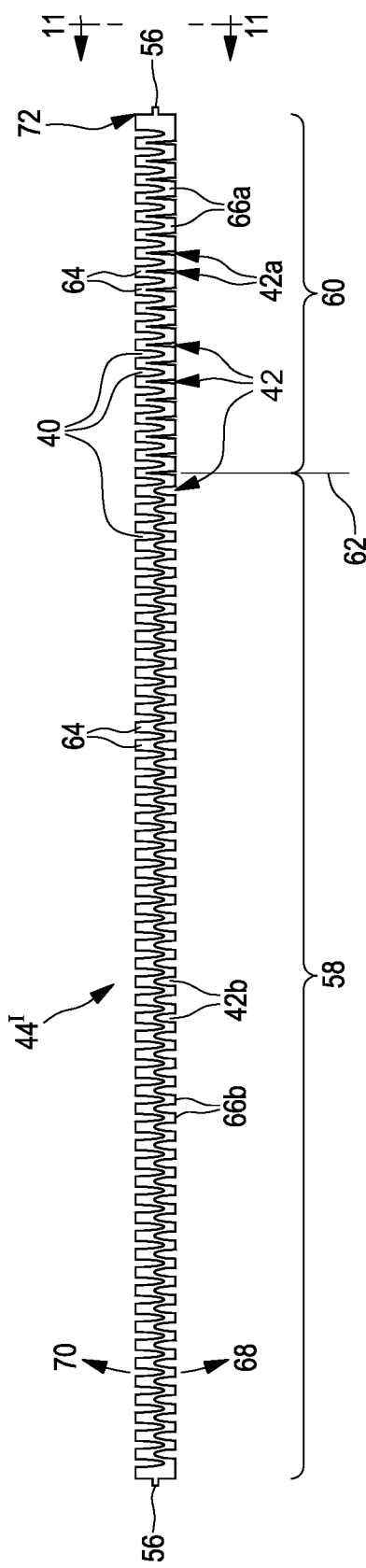
FIG. 10 is a side view of a strut according to one embodiment.
Figure 11:
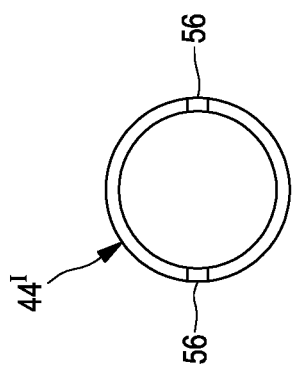
FIG. 11 is an end view of the strut depicted in FIG. 10, taken in the direction of line 11-11 in FIG. 10.

FIG. 10 is a side view of a strut $44^I$ according to an embodiment. FIG. 11 is an end view of the strut depicted in FIG. 10, taken in the direction represented by the arrows on line 11-11 of FIG. 10. In this embodiment, the strut $44^I$ includes a distal part 58 and a proximal part 60 that meet at a location represented by a vertical line 62. Each end of this strut again includes a pair of diametrically-opposed alignment tabs 56, two of which may be seen in FIG. 11. Again, although any number of alignment tabs may be used, it works well to have two alignment tabs that are diametrically opposed from each other as shown to best advantage in FIG. 11. As shown in FIG. 10, in this embodiment of the strut $44^I$, a first plurality of slots 40 are formed in the upper surface of the strut and define a first plurality of arches 64. A second plurality of slots 42 is cut in the bottom surface of the strut $44^I$, creating a second plurality of arches 66. These slots and arches are explained further below.

In the embodiment depicted in FIG. 10, each slot 40 comprising the first plurality of slots is the same, and each arch 64 comprising the first plurality of arches is the same. The second plurality of slots 42, however, comprises two types of slots. In particular, the proximal end of the strut (i.e., the right-hand end of the strut as oriented in FIG. 10) includes a plurality of deep (or tall), narrow cuts or slots 42a, and the distal portion of the strut includes a plurality of relativity wider and more shallow slots 42b. Also, the slots 40 in the top portion of the strut $44^I$ are identical to the slots 42b in the bottom portion of the strut along the distal portion 58 of the strut $44^I$. The differences between the slot configurations in the top of the strut versus the slot configurations in the bottom of the strut along the proximal part of the strut, create asymmetric curves when the catheter is deflected in different directions. In particular, if the distal end of the distal deflectable section is deflected downwardly (i.e., in the direction of arrow 68 depicted in FIG. 10), the deflection curve will tend to commence at the location represented by the vertical line 62, which, as noted above, is at the junction of the distal part 58 with the proximal part 60 of the strut 44'. However, if the distal deflectable section is deflected upwardly (i.e., in the direction of arrow 70 depicted in FIG. 10), the resulting curve will tend to commence closer to the proximal end 72 of the strut.

The strut 44' depicted in FIG. 10 could be created in an automated process. In order to drive the automated process, a cut pattern 74 may be defined from a CAD model of the strut and then information about the design may be loaded into the guidance system for a cutting machine (e.g., a laser cutter—not shown). FIG. 12 depicts a two-dimensional, flat pattern 74 that could be used to direct the cutting machine to create the strut depicted in FIG. 10. In particular, if the flat pattern 74 were formed into a cylindrical configuration (as shown in FIGS. 10 and 11), by joining the top horizontal edge 76 of the pattern depicted in FIG. 12 with the bottom edge 80 of the pattern, that body would have a configuration similar to that shown in FIG. 10.

The pattern 74 depicted in FIG. 12 is symmetrical about a longitudinally-extending line 78, which longitudinally divides the pattern into symmetrical upper and lower halves. That is, the portion of the pattern above the line 78 is a mirror image of the portion of the pattern below the line. This pattern also defines the proximal part 60 (which, in this embodiment, is an asymmetric portion), which is the portion of the pattern to the left of a vertical line 62; and the distal part 58 (which, in this embodiment, is a symmetric portion), which is the portion of the pattern to the right of the vertical line 62. In this embodiment, the first plurality of elliptical slots is longitudinally-arranged (or 'stacked') along the line of symmetry 78. Each elliptical slot 40 in the first plurality of slots is the same. In other words, in the pattern 74 depicted in FIG. 12, the elliptical cutouts comprising the first plurality of slots are the same from the proximal end of the strut to the distal end of the strut.

The pattern depicted in FIG. 12 also comprises a second plurality of cutout regions (or slots) 42. It should be kept in mind that FIG. 12 depicts a 'flat pattern.' Thus, half of each slot in the second plurality of slots opens upwardly in the depicted pattern, and the other half of each slot opens downwardly in the depicted pattern. As may be clearly seen in FIG. 12, the second plurality of slots 42 are not uniform from one end of the strut to the other. In particular, on the proximal end of the strut pattern (i.e., on the left-hand end of the strut pattern as oriented in FIG. 12), along what will become the asymmetric portion of a strut (i.e., the portion to the left of vertical line 62), the second slots 42a are of a first type; and, on the distal end of the strut pattern (i.e., on the right-hand end of the strut pattern as oriented in FIG. 12), along the symmetric portion of the strut pattern (i.e., the portion to the right of vertical line 62), the second slots 42b are of a second type. The second slots of a first type 42a are relatively narrow and relatively long compared to the second slots of a second type 42b along the symmetric portion of the strut. Further, in the symmetric section, the slots in the first plurality of slots are identical to the second type of second slots. That is, to the right of vertical line 62, the complementary slots 40, 42b are the same and are merely staggered longitudinally.

Moving distally from the proximal end of the strut to the distal end of the strut depicted in FIG. 12, the second slots get shorter and wider (e.g., compare slots 42a to slots 42b). In particular, the second slots of the first type 42a are narrow and deep compared to the second slots of the second type 42b. As a direct result, the first arches 64 (discussed further below in connection with FIG. 14) get longer as one transitions from the asymmetric portion of the cut pattern to the symmetric portion. Correspondingly, again moving from the proximal end of the strut to the distal end of the strut, the second arches 66 get narrower (e.g., compare arches 66a to arches 66b). Finally, as one moves from the proximal end of the strut cut pattern 74 depicted in FIG. 12 to its distal end, the bridges 82 (see FIGS. 13 and 14) that connect the first arches 64 to the second arches 66 get shorter. That is, the bridges in the symmetric deflection portion are shorter than the bridges in the asymmetric deflection portion. Bridges are discussed in detail below in connection with FIG. 14. In the configuration depicted in FIGS. 10 and 12, the first arches 64 match the second arches 66b, and the first slots 40 match the second slots 42b in the symmetric portion 58 of the strut. Thus, in the symmetric portion of a strut, deflection is symmetrical. FIG. 13 is an enlarged view of the circled portion of FIG. 12.

Figure 14:
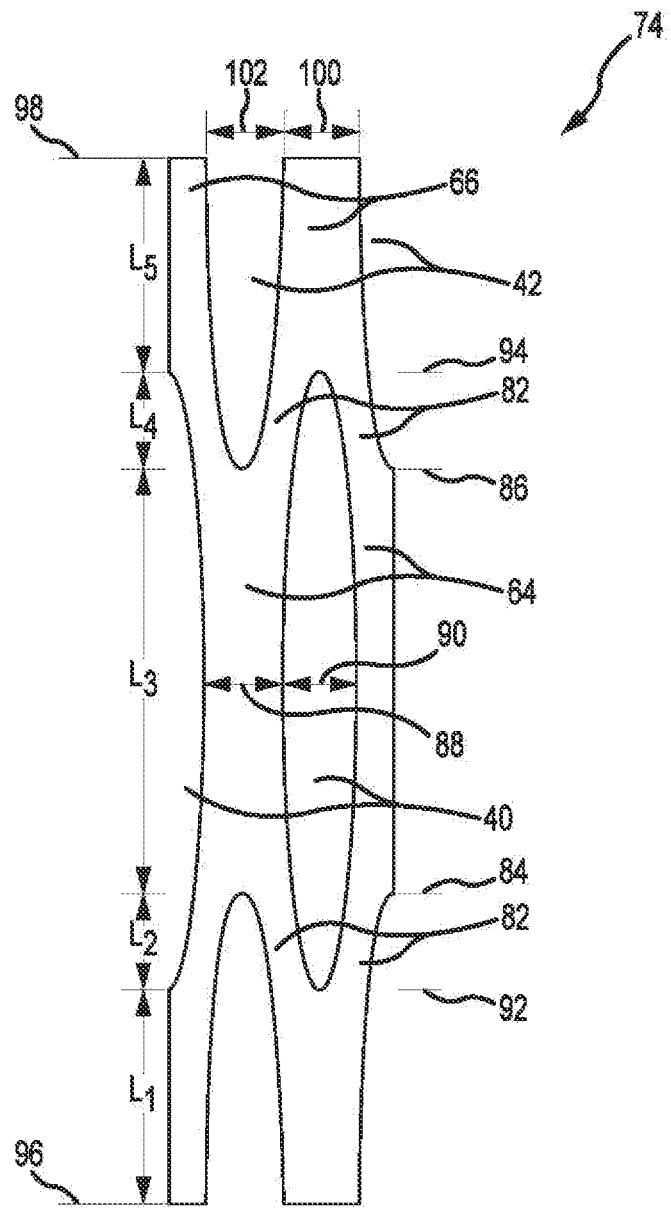
FIG. 14 is a greatly enlarged, fragmentary view of a portion of a cut pattern such as the one depicted in FIG. 12, depicting further details about the construction and components of a strut.

In order to better understand the cut patterns used to form the struts, FIG. 14 depicts a greatly enlarged portion of the cut pattern 74 depicted in FIG. 12. Each strut is formed from a series of longitudinally-offset arches, including a first plurality of arches 64 and a second plurality of arches 66. The arches comprising the first plurality of arches are arranged in a longitudinally-extending row (or series), as shown to good advantage in FIG. 12. Similarly, the arches 64 comprising the second plurality of arches are arranged in a complementary and circumferentially-offset, second longitudinally-extending row. Adjacent arches of said first plurality of arches 64 are separated by circumferentially-extending cutout regions 40 (or slots or channels or gaps). Similarly, adjacent arches 66 comprising the second plurality of arches are separated by circumferentially-extending cutout regions 42. Each cutout region may have an elliptical configuration as shown in, for example, FIG. 12-14, or a cat-eye or almond configuration, such as shown in, for example, FIG. 3. Other symmetrical and asymmetrical slot shapes are contemplated, such as diamonds, rectangles, and triangles.

Figure 15:
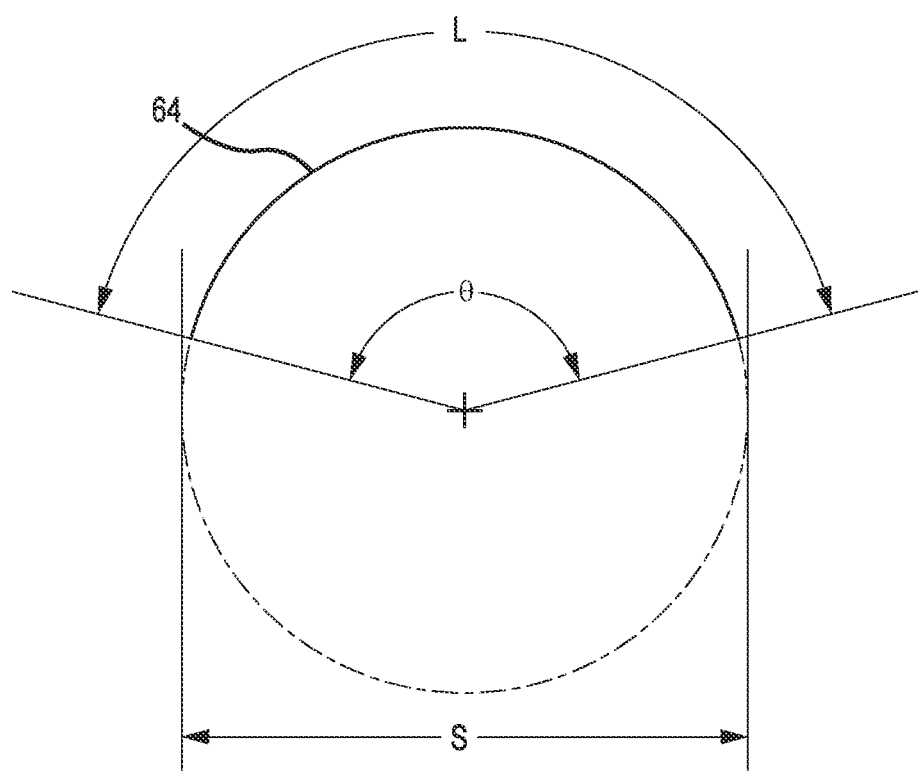
FIG. 15 schematically depicts a representative view of an arch comprising part of a strut, and provides details regarding the parameters used to describe an arch configuration.

Again referring to FIG. 14, each of the first arches 64 extends circumferentially a distance L3 between a third longitudinally-extending line 84 and a fourth longitudinally-extending line 86. Each of these first arches has a midpoint width 88. Further, each of the first arches is separated from the next adjacent arch by a first cutout region 40. Each of the these first cutout regions has its own midpoint width 90, and extends circumferentially a distance L2+L3+L4 between a second longitudinally-extending line 92 and a fifth longitudinally-extending line 94, as clearly depicted in FIG. 14. Referring briefly to FIG. 15, each arch (e.g., arch 64) shown in FIG. 14 subtends an angle theta (θ) and has an arc length L and a span S. Referring back to FIG. 14, the depicted cut pattern 74 further comprises a plurality of second arches 66, each having a mid-point width 100, separated by a plurality of second cutout regions 42, each having a mid-point width 102. Each of the second arches extends circumferentially a distance L1+L5 from the second longitudinally-extending line 92 in FIG. 14 to the fifth longitudinally-extending line 94, keeping in mind that the cut pattern 74 depicted in FIG. 14 is a flat, two-dimensional pattern. Thus, the first longitudinally-extending line 96 and the sixth longitudinally-extending line 98 shown in FIG. 14 comprise the same line in the cylindrical strut 44' formed from the pattern depicted in FIG. 14. Thus, the length of the second arches, as discussed above, is the distance L1 from the second longitudinally-extending line 92 downward (as depicted in FIG. 14) to the first longitudinally-extending line 96, plus the distance L5 from the fifth longitudinally-extending line 94 upward (as depicted in FIG. 14) to the sixth longitudinally-extending line 98. As also shown in FIG. 14, the length of each second cutout region 42 in this particular pattern is the sum of L1+L2+L4+L5.

FIG. 14 also clearly depicts the bridges 82 (or links or connectors) that connect the first arches 64 to the second arches 66. These bridges flexibly interconnect the first plurality of arches to the second plurality of arches. A first plurality of adjacent bridges 82 form a first longitudinally-extending, serpentine backbone (this backbone may be seen in, for example, FIG. 10 running longitudinally along the vertical midline of the strut $44^I$), which permits and facilitates preferentially-planar deflection of the distal deflectable section 20, and restrains out-of-plane deflection. When the slots are elliptical as shown in, for example, FIG. 14, the arches take the shape of necked-in rectangles in the two-dimensional cut pattern.

Figure 16:
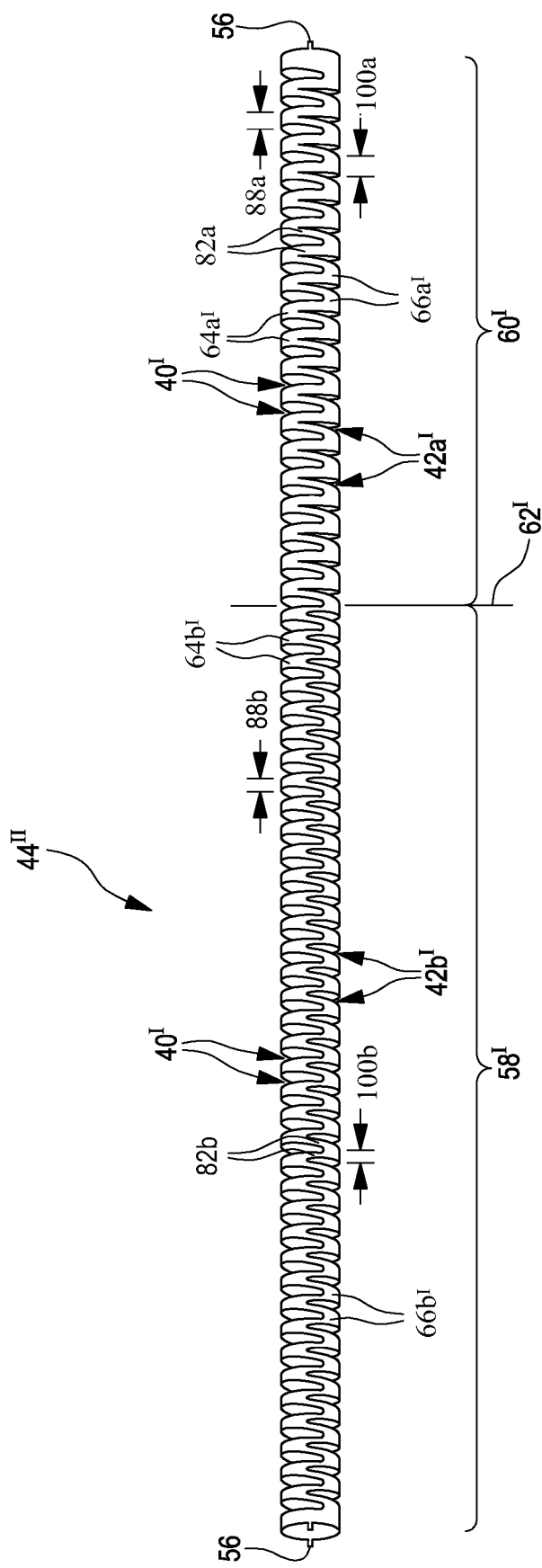
FIG. 16 is an isometric view of a strut according to another embodiment.

FIG. 16 is an isometric view of a strut $44^{II}$ according to another embodiment. In this figure, the distal end of the strut is on the left, and the proximal end of the strut is on the right. Similar to the strut discussed above, the strut depicted in FIG. 16 includes a section $58^I$ of symmetric cuts and a section $60^I$ of asymmetric cuts. In section $58^I$, the top cuts $40^I$ and bottom cuts $42b^I$ are the same. In contrast, in section $60^I$, the top cuts $40^I$ and bottom cuts $42a^I$ are different. Looking more carefully at FIG. 16, a first plurality of slots $40^I$ separates a first plurality of arches $64a^I$, $64b^I$. In the section $58^I$ of the strut, each arch $64b^I$ has a first width $88b$. In section $60^I$, each arch $64a^I$ has a second width $88a$ that is larger than the first width.

Looking now more carefully at the slots on the bottom of the strut $44^{II}$ depicted in FIG. 16, the slots $42b^I$ in section $58^I$ are shallower but wider than the slots $42a^I$ in section $60^I$. Thus, moving distally from the proximal end of the strut to the distal end of the strut (i.e., from right to left in FIG. 16), the first slots $40^I$ remain constant, the first arches get narrower and longer (i.e., arches $64b^I$ are narrower and longer than arches $64a^I$) after the transition from section $60^I$ to section $58^I$ (i.e., after crossing vertical line $62^I$), the second slots get shorter and wider (i.e., slots $42b^I$ are shorter and wider than slots $42a^I$) after the transition from section $60^I$ to section $58^I$, the second arches get narrower (compare width $100a$ of arches $66a^I$ to width $100b$ of arches $66b^I$), and the bridges get shorter (compare longer bridges $82a$ to shorter bridges $82b$).

Figure 17:
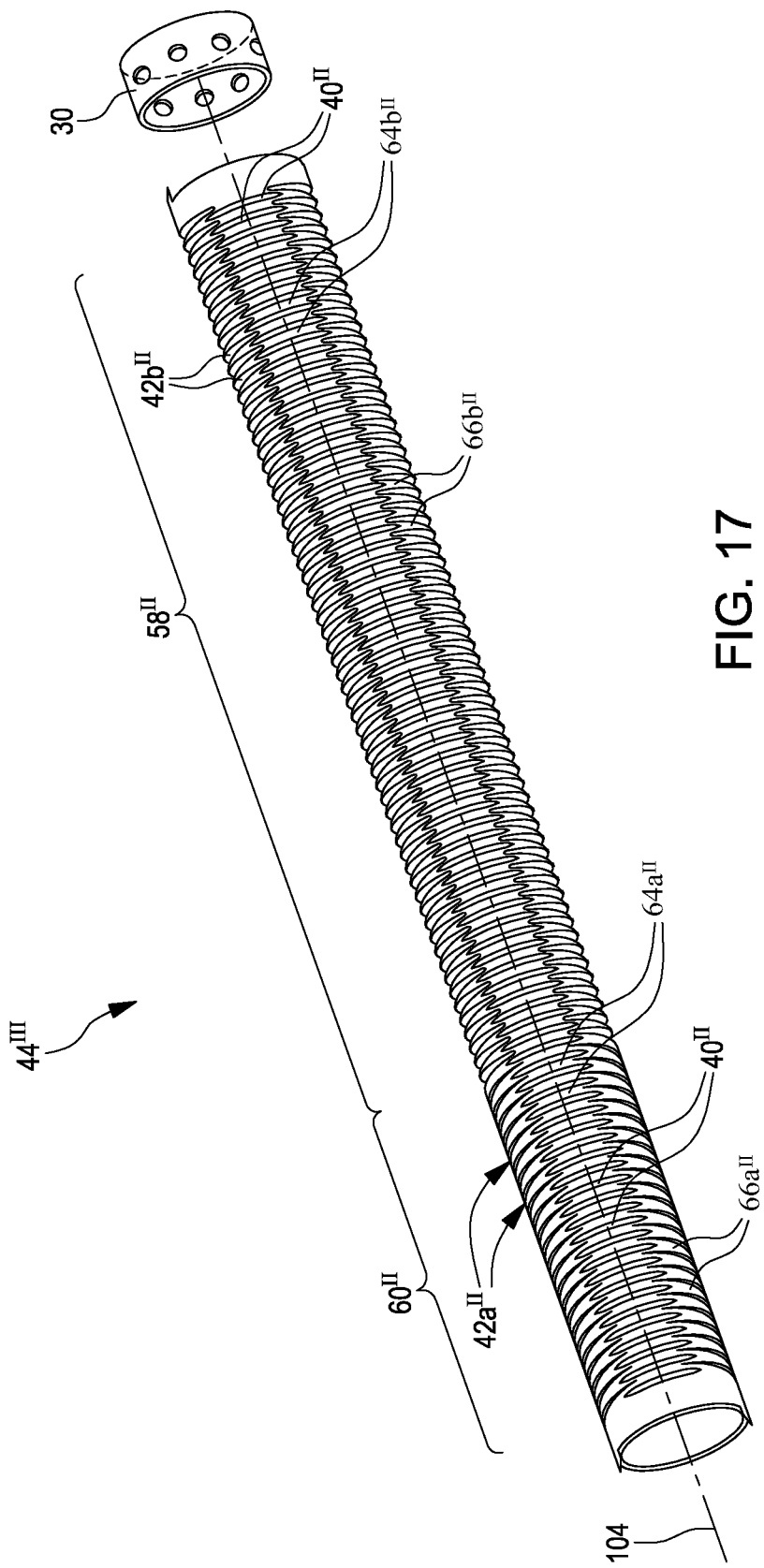
FIG. 17 is an isometric view of another embodiment of a strut, shown adjacent to a representative pull ring.

FIG. 17 depicts yet another embodiment of a strut $44^{III}$. FIG. 17 also shows a pull ring 30 exploded away from the distal end of the strut. The strut depicted in FIG. 17 has a stiffer proximal portion $60^{II}$ (i.e., the left end of the strut as depicted in FIG. 17) and a softer distal portion $58^{II}$ (i.e., the right end of the strut as depicted in FIG. 17). The strut again comprises a first plurality of arches $64a^{II}$, $64b^{II}$, a first plurality of slots $40^{II}$, a second plurality of arches $66a^{II}$, $66b^{II}$ and a second plurality of slots $42a^{II}$, $42b^{II}$. The first plurality of slots $40^{II}$ and the first plurality of arches $64a^{II}$, $64b^{II}$ are arranged along a first longitudinally-extending line 104 in FIG. 17. In other words, the midpoints (or waists) of the first plurality of slots $40^{II}$ and of the first plurality of arches $64b^{II}$ would be aligned along the first longitudinally-extending line 104. In this particular embodiment, the slots in the first plurality of slots $40^{II}$ remain a constant size for the entire length of the strut $44^{III}$. The slots in the second plurality of slots $42a^{II}$, $42b^{II}$, however, are shorter and wider in the softer section $58^{II}$ of the strut than they are in the stiffer section $60^{II}$ of the strut. In this embodiment, the midpoints of the second plurality of slots $42a^{II}$, $42b^{II}$ and of the second plurality of arches $66a^{II}$, $66b^{II}$ would be aligned along a second longitudinally-extending line (not shown in FIG. 17) that would be circumferentially offset 180 degrees from the first longitudinally-extending line 104. Since the second slots get shorter in the distal, softer portion $58^{II}$ of the strut $44^{II}$ depicted in FIG. 17 (compare longer slots $42a^{II}$ to shorter slots $42b^{II}$), the first arches get longer in the softer, distal portion $58^{II}$ (compare longer arches $64b^{II}$ to shorter arches $64a^{II}$). The second arches $66a^{II}$, $66b^{II}$, however, remain the same length size throughout the length of the strut $44^{III}$. Finally, as one moves distally and transitions from the stiffer portion $60^{II}$ to the softer portion $58^{II}$, the bridges get shorter. That is, the bridges are shorter in the softer portion of the strut.

Looking next at FIGS. 18-20, some relatively complex strut cut patterns $74^I$, $74^{II}$, $74^{III}$, respectively, each for creating a strut having longitudinally-varying stiffness, are described next. Each of these cut patterns comprises twelve sections (S1-S12—only labeled in FIG. 18) and eight different sub-cut patterns (P1-P8—only labeled in FIG. 18), but any number of sections and sub-cut pattern combinations could be used. Further, each strut pattern depicted in FIGS. 18-20 includes a proximal pattern portion 106 (to the left of vertical line 108) and a distal pattern portion 110 (to the right of vertical line 108). The proximal pattern portion 106 is the same for each of these three strut cut patterns $74^I$, $74^{II}$, $74^{III}$, and comprises six sections (namely, S1-S6) and five sub-cut patterns (namely, P1-P5):

Section S1 comprises sub-cut pattern P1;
Section S2 comprises sub-cut pattern P2;
Section S3 comprises sub-cut pattern P3;
Section S4 comprises sub-cut pattern P4;
Section S5 comprises sub-cut pattern P4; and
Section S6 comprises sub-cut pattern P5.

Figures 18, 19, 20:
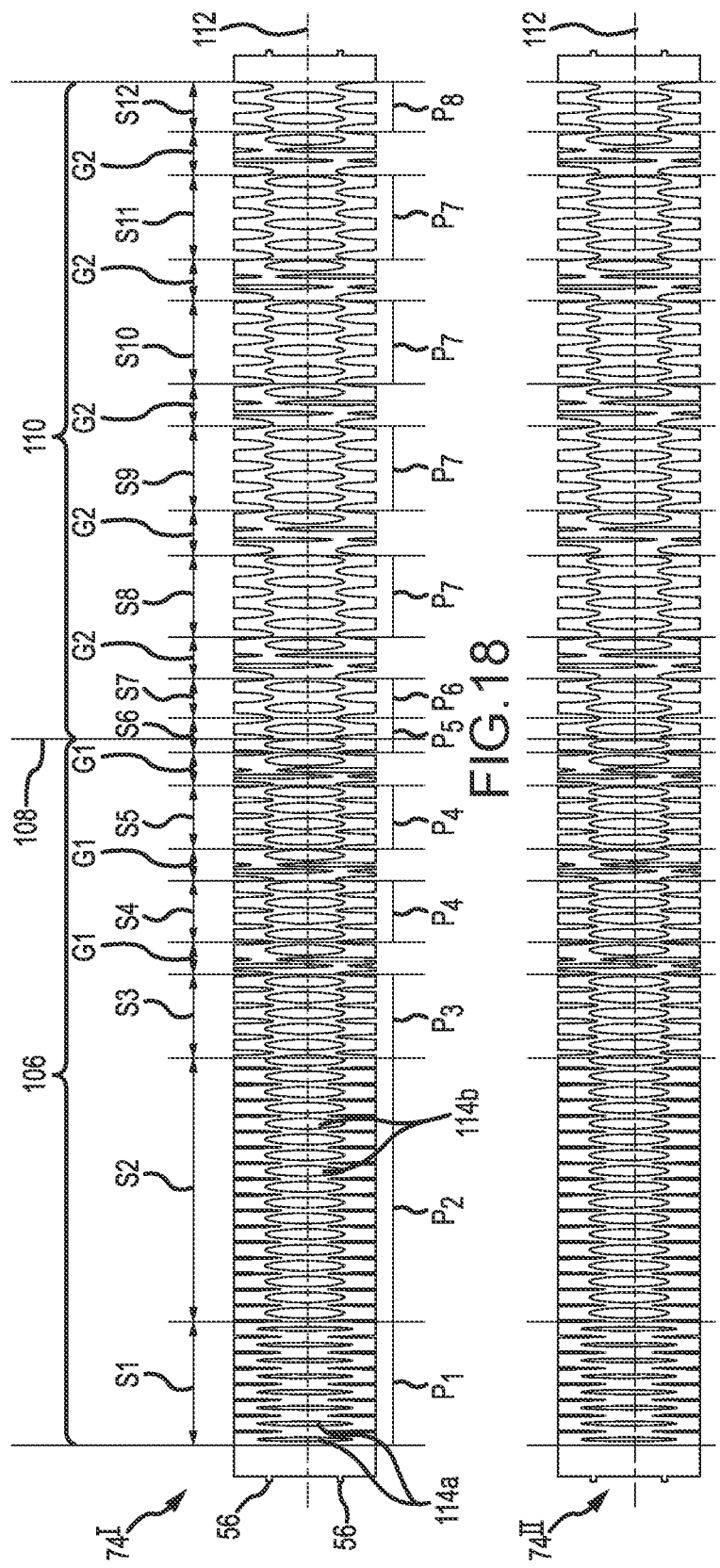
FIGS. 18-20 depict different embodiments of two-dimensional cut patterns that could be used to form various strut embodiments, each having stiffness that varies along the longitudinal axis of the strut.

Each of the distal strut pattern portions 110 shown in FIGS. 18-20 is different from the other two, and each again comprises six sections (namely S7-S12), but only three cut patterns (namely, P6-P8):

Section S7 comprises sub-cut pattern P6;
Section S8 comprises sub-cut pattern P7;
Section S9 comprises sub-cut pattern P7;
Section S10 comprises sub-cut pattern P7;
Section S11 comprises sub-cut pattern P7; and
Section S12 comprises sub-cut pattern P8.

Continuing to consider FIGS. 18-20, the following pairs of adjacent sections are separated by a type one expansion gap (or transition region), G1, or a type two expansion gap, G2 (these gaps G1, G2 are only labeled in FIG. 18):

Sections S3 and S4 are separated by expansion gap G1;
Sections S4 and S5 are separated by expansion gap G1;
Sections S5 and S6 are separated by expansion gap G1;
Sections S7 and S8 are separated by expansion gap G2;
Sections S8 and S9 are separated by expansion gap G2;
Sections S9 and S10 are separated by expansion gap G2;
Sections S10 and S11 are separated by expansion gap G2; and
Sections S11 and S12 are separated by expansion gap G2.

As noted above and as may be clearly seen in these three figures, the G1 expansion gap is different from the G2 expansion gap G2.

As already stated, section S1-S6, which together comprise the proximal strut cut pattern portion 106, are the same in each of the cut patterns $74^I$-$74^{III}$ depicted in FIGS. 18-20, respectively. In particular, in the proximal strut cut pattern portion 106, the slots straddling the longitudinal centerline 112 that bifurcates the pattern horizontally into symmetrical upper and lower portions are long and narrow in the section S1 (see slots 114a), and then wider (longer midpoint width) and shorter in remaining sections S2-S6 (see slots 114b). The slots 114b in section S2-S6 are the same size in the depicted embodiment.

On the other hand, the distal portion 110 of the cut patterns depicted in FIGS. 18-20 is different in each figure. In FIG. 18, the first slots, which extend along the longitudinal centerline 112 are the same size in all of sections S7-S12 (in fact, in FIG. 18, the first slots are the same size in all of sections S2-S12). In contrast, in FIGS. 19 and 20, the first slots are not all the same size in sections S7-S12. In the FIG. 19 cut pattern, the slots (which are part of the first plurality of slots) in section S7 through section S12 are longer (i.e., taller in FIG. 19) than they are in sections S2-S6. Similarly, in the FIG. 20 cut pattern, the slots (which are again part of the first plurality of slots) in section S7 through S12 are even longer than the corresponding slots in FIG. 19. Thus, a strut constructed from the strut cut pattern $74^I$ depicted in FIG. 18 would have the stiffest distal strut portion, a strut constructed from the strut cut pattern $74^{III}$ depicted in FIG. 20 would have the least stiff distal strut portion, and a strut constructed from the strut cut pattern $74^{II}$ depicted in FIG. 19 would have a stiffness somewhere between the stiffness of the other two. As should be apparent from reviewing the representative cut patterns depicted in FIGS. 18-20, struts created from these patterns can flex section-by-section, mitigating the tendency of the deflectable section to come out of plane during deflection. These cut patterns also result in a preferentially-planar performance.

Figure 21:
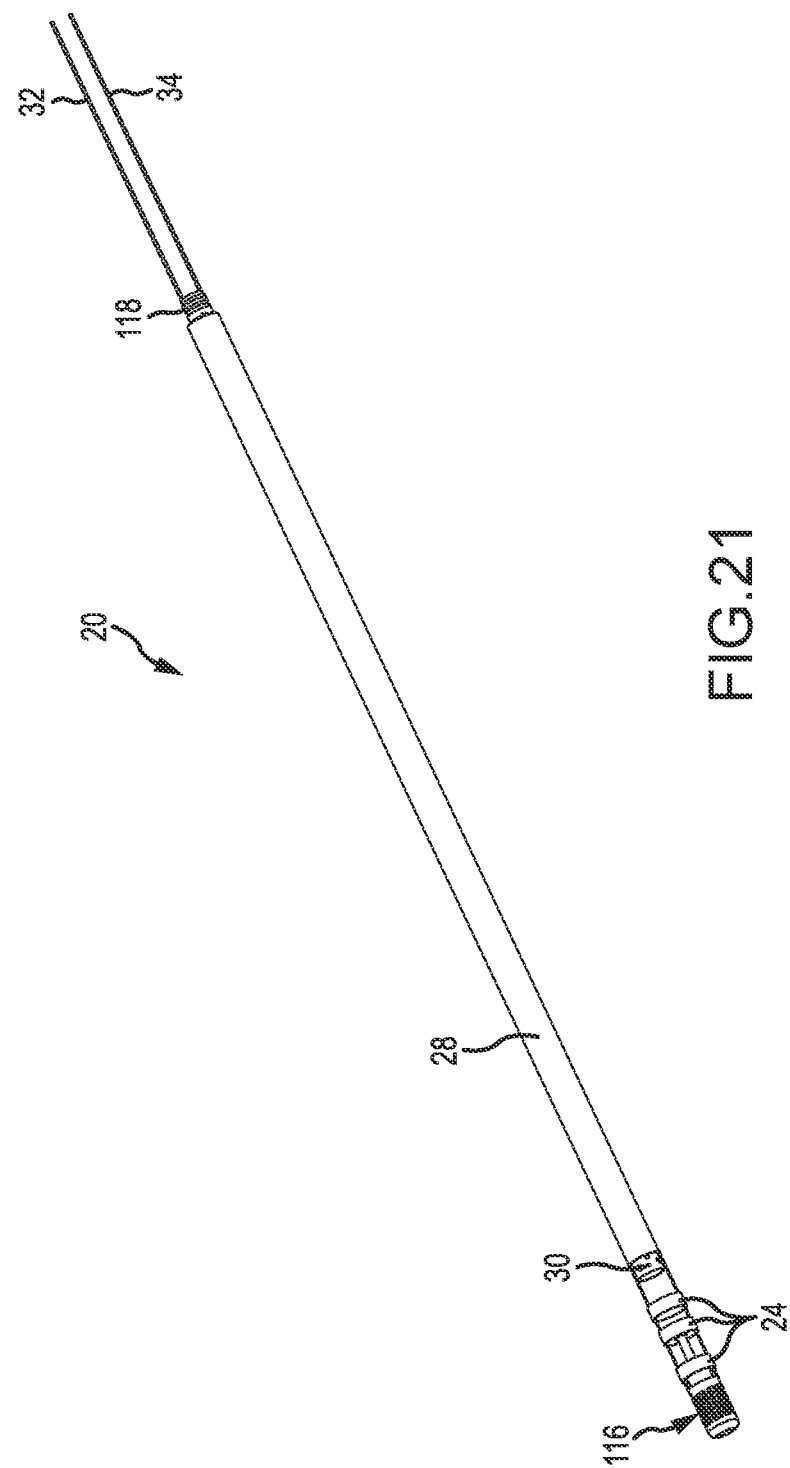
FIG. 21 is a fragmentary, isometric view of a representative distal deflectable section of an ablation catheter having a flexible, irrigation tip, a strut assembly, and a coupler for attaching the distal deflectable section to a proximal catheter shaft.

FIG. 21 is a fragmentary, isometric view of a distal deflectable section 20 of an ablation catheter, shown with portions removed or displaced to reveal various internal components. In this figure, a flexible, irrigated tip electrode 116 is shown distal of three ring electrodes 24 and a pull ring 30. Also visible in this figure, at the proximal end of the distal deflectable section 20, is a coupler 118 that may be used to join the distal deflectable section 20 to the proximal catheter shaft 18.

Figure 22:
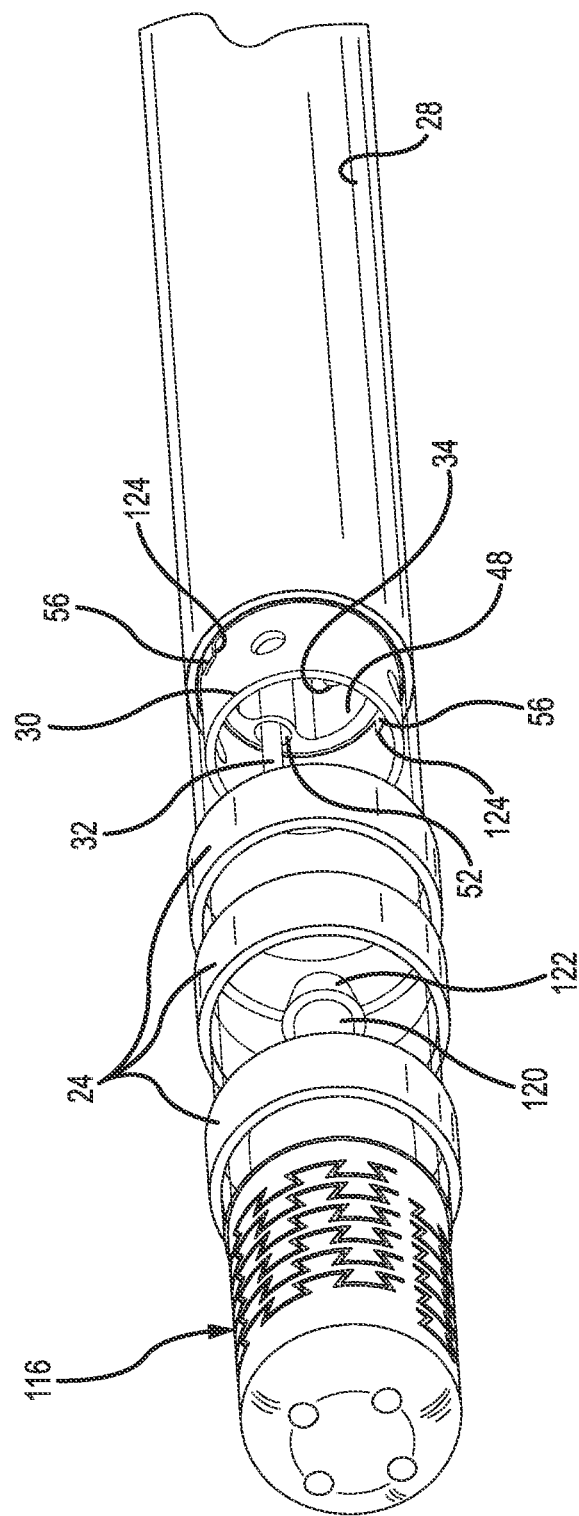
FIGS. 22 and 23 are enlarged, fragmentary views of the distal portion of the distal deflectable section depicted in FIG. 21, and provide further details about the placement of various components.
Figure 23:
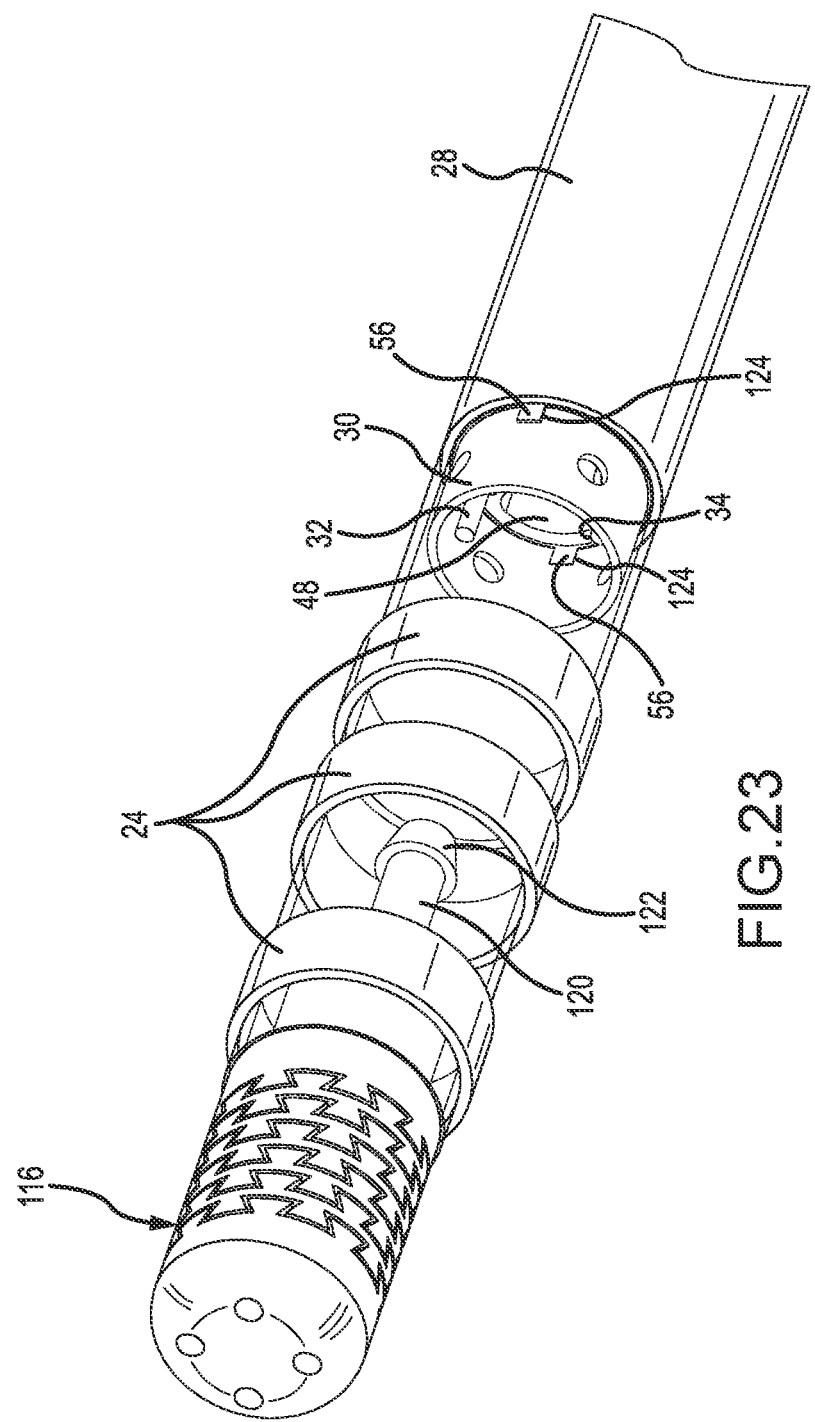

FIGS. 22 and 23 are enlarged, fragmentary isometric views of part of the distal portion of the distal deflectable section shown in FIG. 21. As shown on these two figures, the flexible irrigated tip electrode includes a tip irrigation tube 120 with a barb 122 on its proximal end for connection to a shaft irrigation tube (not shown). Three ring electrodes 24 are shown 'hovering' in approximately the correct longitudinal position. A respective pull ring 30 is visible in each of these two figures. Also highly visible in each of these two figures are the alignment tabs 56 riding in corresponding tab slots 124 in the pull ring to ensure that the pull wires 32, 34 and the pull wire management channels 52, 54 are properly aligned with the cut pattern in the strut.

Figure 24:
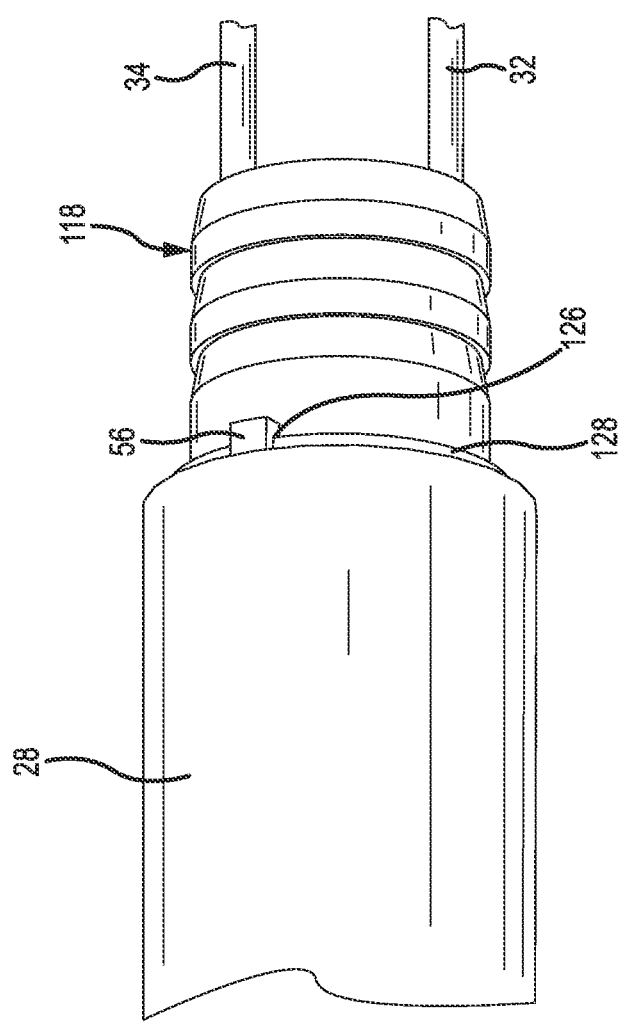
FIGS. 24 and 25 are enlarged, fragmentary, isometric views of the proximal portion of the distal deflectable section depicted in FIG. 21, and show the alignment tabs in position on a tab alignment ring comprising part of one possible embodiment of a coupler.
Figure 25:
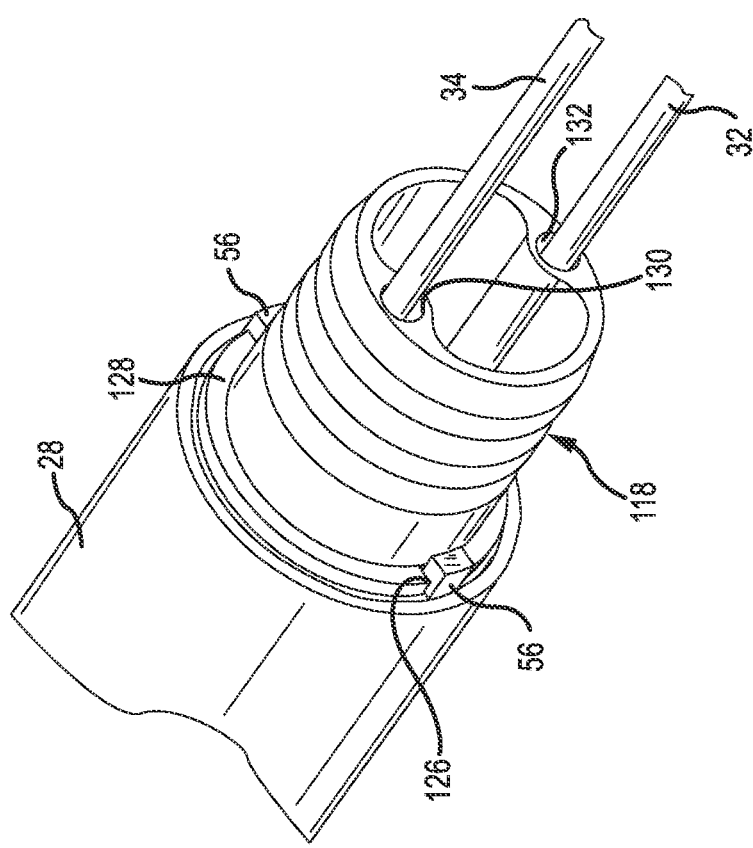
Figure 26:
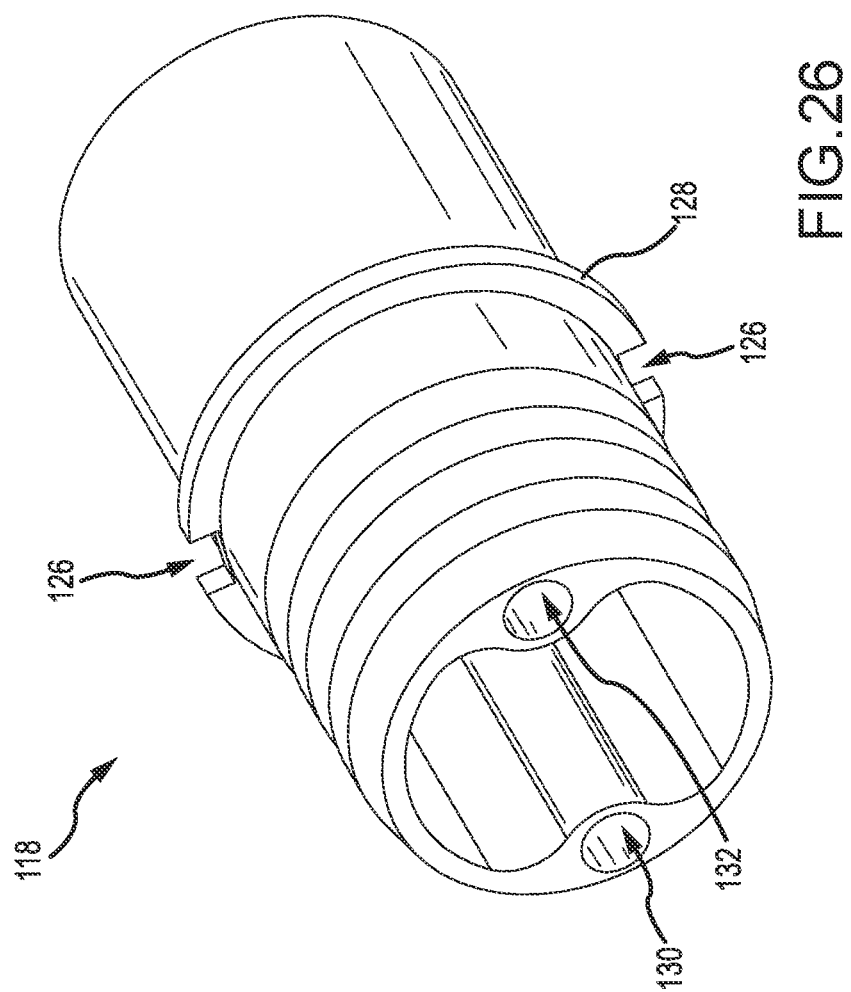
FIGS. 26 and 27 are enlarged, isometric views of the coupler that is also depicted in FIGS. 21, 24, and 25.
Figure 27:
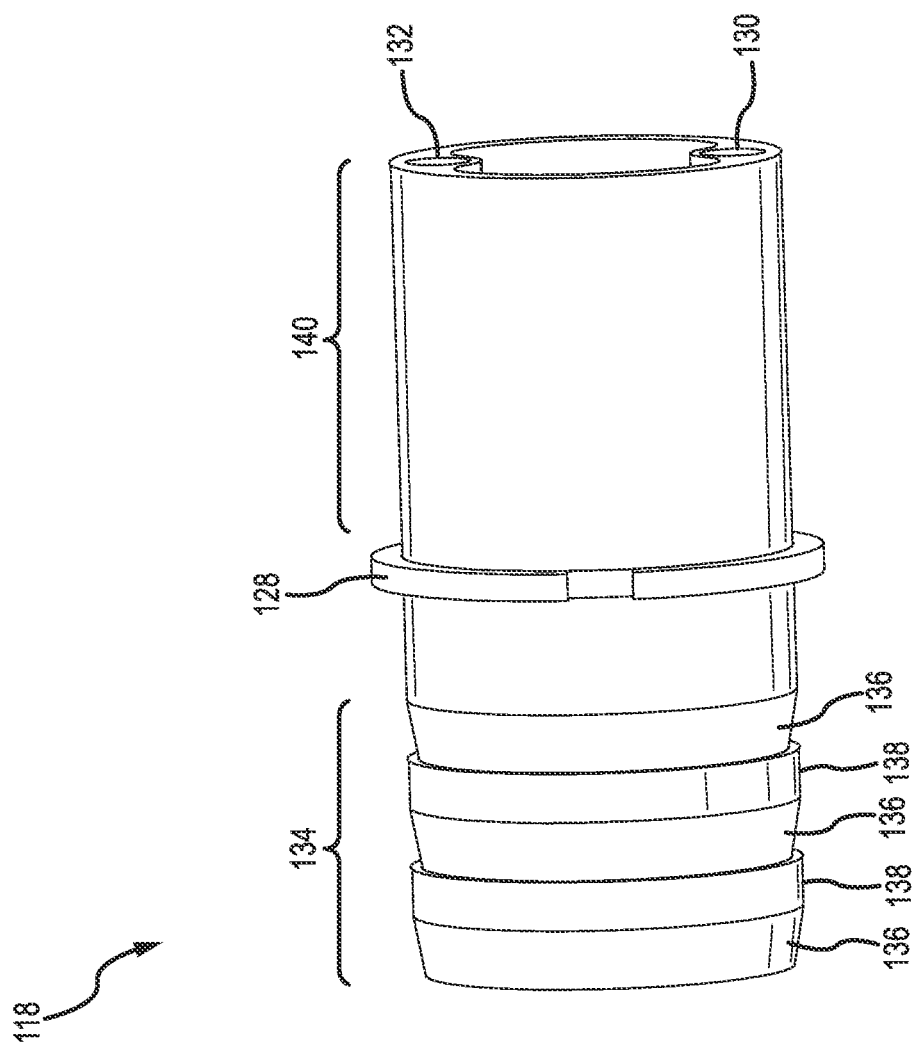

Referring next to FIGS. 24-27, the coupler 118 that is also depicted in FIG. 21 will be described. FIGS. 24 and 25 are fragmentary, isometric views of the proximal end of the distal deflectable section depicted in FIG. 21. In each of these two figures, it is possible to see a coupler 118 extending from the proximal end of the distal deflectable section. The distal end of the coupler (not shown in FIGS. 24 and 25) would ride adjacent to or against the proximal end of the strut comprising part of the strut assembly. As clearly shown in these figures, the alignment tabs 56 extending proximally from the proximal end of the strut ride in tab slots 126 formed in a tab alignment ring 128 comprising part of the coupler 118. These tab slots and the tab alignment ring may be clearly seen in FIG. 26 as well. In FIGS. 24 and 25, the pull wires 32, 34 are shown schematically entering the pull wire channels 130, 132 comprising part of the shaft coupler 118. These pull wires would be connected on their distal ends to, for example, the pull ring 30, and would be connected on their proximal ends to an actuator. The pull wire channels 130, 132 would align with the similar pull wire channels 52, 54 comprising part of the insert component 48 that is part of the strut assembly 46. Also clearly visible in FIGS. 24-27 is a barbed section 134 (labeled in FIG. 27) of the coupler 118. This barbed section comprises a plurality of slopped annular sections 136 and flat annular sections 138. The barbed section 134 would be inserted into the distal end of the proximal catheter shaft 18 and then would be connected by adhesive or sonic welding or some other means to the proximal catheter shaft. The pull wire channels 130, 132 are offset 90 degrees from the tab slots 126. The end of the coupler 118 opposite the barbed section 134 comprises a smooth section 140. This smooth section 140 would ride in, and be attached to, the proximal end of the distal deflectable section 20.

Figure 28:
FIGS. 28-30 schematically depict a distal deflectable section comprising a strut assembly before a severe kink, while having a severe kink, and after recovering from a severe kink.
Figure 29:
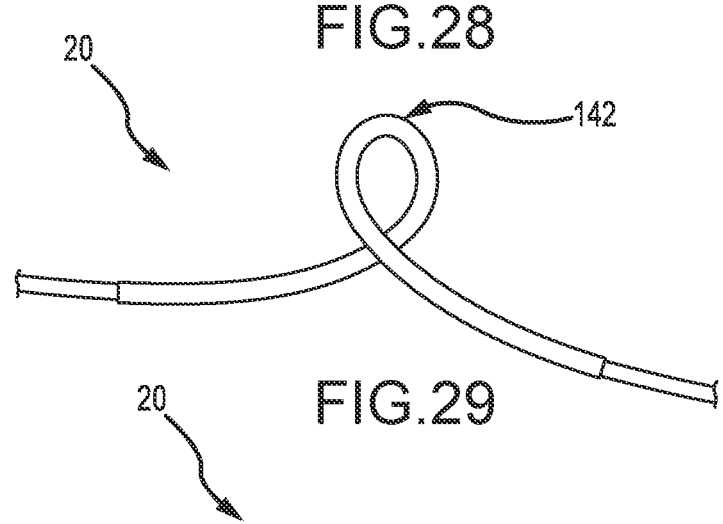
Figure 30:

FIG. 28 schematically shows a distal deflectable section 20. FIG. 29 schematically depicts the distal deflectable section of FIG. 28 with a severe kink 142 formed in it. FIG. 30 shows that, after the kink has been removed, the distal deflectable section recovers from even such a severe kink when the strut assembly described herein is in place.

The strut described above, whether constructed from a laser cut Nitinol tube or some other material, can be configured to give control over the deflection characteristics of a catheter, especially asymmetric deflection, while maintaining the orientation of internal components. The design of the cut pattern can be altered to create various asymmetric curve shapes, planar behavior, desired curve sizes, and desired catheter shaft stiffness.

One of the benefits of this curve strut is that it makes manufacturing of, for example, the distal deflectable section of a catheter easy and repeatable. Current manufacturing practices may introduce potentially undesirable variability in outgoing assemblies due to the difficult and labor-intensive process required to produce a given deflection behavior. The strut describe about is designed to have an inherent deflection behavior that is easy to assemble and lacks the variation in other assembly methods. The strut helps the catheter take that shape in each deflection. This takes much of the variability out of creating a distal deflectable section by creating a structure with which to create the deflection behavior. Additionally, this component provides excellent durability in the body due to the fact that it does not degrade under in vivo conditions and the super elastic nature of the Nitinol provides excellent return to straight ability in a catheter application.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

Reference throughout the specification to "various embodiments," "some embodiments," "one embodiment," or "an embodiment," or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial or directional terms such as "vertical," "horizontal," "up," "down," "clockwise," and "counterclockwise" may be used herein with respect to the illustrated embodiments. However, medical instruments may be used in many orientations and positions, and these terms are not intended to be limiting and absolute.

Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relation to each other. As used herein, joinder references may also include two components that are molded as a single or unitary piece. Changes in detail or structure may be made without departing from the spirit of the disclosure as defined in the appended claims.

What is claimed is:

1. A catheter curve shape strut comprising the following:
   a longitudinally-extending cylindrical wall, the wall having an outer surface, an outer surface circumference, and an outer surface length measured longitudinally, wherein the wall comprises connected end-to-end cylindrical sections including at least a first cylindrical section and a second cylindrical section;
   a plurality of first slots through the wall and sequentially arranged along a first line extending longitudinally along the wall outer surface in both the first cylindrical section and the second cylindrical section; and
   a plurality of second slots through the cylindrical wall and sequentially arranged along a second line extending longitudinally along the wall outer surface in both the first cylindrical section and the second cylindrical section, wherein the second line is circumferentially offset from the first line by 180 degrees, wherein the plurality of second slots are longitudinally offset from the plurality of first slots, wherein the plurality of second slots further comprises second slots of a first shape and second slots of a second shape different from the first shape, wherein the second slots of the first shape are sequentially arranged along the second line only along the first cylindrical section, wherein the second slots of the second shape are sequentially arranged along the second line only along the second cylindrical section, and wherein the first shape is configured to deflect the first section at a first curvature and the second shape is configured to deflect the second section at a second curvature that is different than the first curvature;
   wherein the strut is configured to bend asymmetrically in different directions from a longitudinal axis of the strut based on a shape of the first slots and based on the first and second shapes of the second slots; and
   wherein the end-to-end cylindrical sections further include a third cylindrical section and a fourth cylindrical section, wherein the third and fourth cylindrical sections are separated by an expansion gap, the expansion gap including a third slot extending through the cylindrical wall, wherein the third slot has a third slot length measured circumferentially on the outer surface, wherein the third slot length is greater than a first slot length of each of the plurality of first slots measured circumferentially on the outer surface and a second slot length of each of the plurality of second slots measured circumferentially on the outer surface.

2. The catheter curve shape strut of claim 1, wherein the second slots of the second shape are longer in a circumferential dimension than one-half of the outer surface circumference, and wherein at least some of the second slots of the second shape circumferentially overlap with at least some of the plurality of first slots.

3. The catheter curve shape strut of claim 1, wherein a shape of the first slots is the same as the second slots of the second shape.

4. The catheter curve shape strut of claim 1, wherein the first cylindrical section comprises a first sub-cut pattern, the second cylindrical section comprises a second sub-cut pattern, the third cylindrical section comprises a third sub-cut pattern, and the fourth cylindrical section comprises a fourth sub-cut pattern, and wherein each of the first, second, third, and fourth sub-cut patterns includes a pattern of the plurality of first slots and the plurality of second slots that is different than at least one of the other first, second, third, and fourth sub-cut patterns.

5. A catheter curve shape strut configured to facilitate preferentially-planar, asymmetric deflection of a medical device, the catheter curve shape strut comprising the following:
   a longitudinally-extending cylindrical wall, the wall having an outer surface, an outer surface circumference, and an outer surface length measured longitudinally, wherein a first line extends longitudinally along the outer surface, wherein a second line extends longitudinally along the outer surface, and wherein the second line is circumferentially offset from the first line by 180 degrees;
   a plurality of first slots through the cylindrical wall and sequentially present along the first line, wherein each first slot has a first slot length measured circumferentially on the outer surface between first slot ends, wherein each first slot has a first slot width measured longitudinally on the outer surface, and wherein the first slot length is greater than the first slot width;
   a plurality of first arches, wherein each first arch is present between a pair of longitudinally-adjacent first slots, wherein each first arch has a first arch length measured circumferentially on the outer surface, wherein each first arch has a first arch width measured longitudinally on the outer surface, and wherein the first arch length is greater than the first arch width;

a plurality of second slots through the cylindrical wall and sequentially present along the second line, wherein each second slot has a second slot length measured circumferentially on the outer surface between second slot ends, wherein each second slot has a second slot width measured longitudinally on the outer surface, and wherein the second slot length is greater than the second slot width; and a plurality of second arches, wherein each second arch is present between a pair of longitudinally-adjacent second slots, wherein each second arch has a second arch length measured circumferentially on the outer surface, wherein each second arch has a second arch width measured longitudinally on the outer surface, and wherein the second arch length is greater than the second arch width;

a plurality of bridges connecting the first arches to the second arches, wherein the plurality of bridges define a first serpentine backbone and a second serpentine backbone;

a first expansion gap including a third slot extending through the cylindrical wall, the first expansion gap dividing one of the first or the second serpentine backbones, wherein the third slot has a third slot length measured circumferentially on the outer surface, wherein the third slot length is greater than the first slot length of the plurality of first slots and the second slot length of the plurality of second slots;

wherein at least one of the first slot length and the second slot length is greater than one-half of the outer surface circumference.

6. The catheter curve shape strut of claim 5 further comprising a second expansion gap, wherein the first expansion gap divides the first serpentine backbone and the second expansion gap divides the second serpentine backbone.

7. The catheter curve shape strut of claim 5, wherein the expansion gap length is greater than three-quarters of the outer surface circumference.

8. The catheter curve shape strut of claim 5, wherein each slot of the plurality of first slots is elliptical.

9. The catheter curve shape strut of claim 5, wherein each slot of the plurality of first slots is cat-eye shaped.

10. The catheter curve shape strut of claim 5, wherein each slot of the plurality of first slots is almond shaped.

11. The catheter curve shape strut of claim 5, wherein each slot of the plurality of first slots is identical.

12. The catheter curve shape strut of claim 11, wherein each arch of the plurality of first arches is identical.

13. The catheter curve shape strut of claim 5, wherein the plurality of second slots comprises a plurality of second slots of a first shape and a plurality of second slots of a second shape.

14. The catheter curve shape strut of claim 13, wherein the plurality of second slots of the first shape are sequentially present along the second line, wherein the plurality of second slots of the second shape are sequentially present along the second line, and wherein the plurality of second slots of the first shape have a second slot width that is greater than a second slot width of the plurality of second slots of the second shape.

15. The catheter curve shape strut of claim 13, wherein the plurality of second slots of the first shape are shaped and dimensioned the same as the plurality of first slots.

16. The catheter curve shape strut of claim 5, wherein each of the the plurality of second slots are shaped and dimensioned the same as each of the plurality of first slots.

17. The catheter curve shape strut of claim 5, wherein the plurality of first slots and the plurality of second slots are configured such that the catheter strut is adapted to take a first shape when deflected in a first direction, and to take a second shape when deflected in a second, opposite direction.

18. The catheter curve shape strut of claim 17, wherein the first shape is the same the second shape.

19. The catheter curve shape strut of claim 5, wherein the catheter strut is adapted to deflect in first and second directions both lying within a single imaginary plane, and wherein the plurality of first slots and the plurality of second slots are selected such that the catheter strut deflects asymmetrically in the first and second directions.

20. The catheter curve shape strut of claim 5, wherein the catheter strut is constructed from a super-elastic Nitinol.

21. The catheter curve shape strut of claim 5 further comprising at least two alignment tabs on each longitudinal end of the strut.

22. The catheter curve shape strut of claim 5 further comprising two diametrically-opposed alignment tabs on a longitudinal end of the strut.

23. A catheter curve shape strut assembly comprising the following:
a curve shape strut comprising the following:
a longitudinally-extending cylindrical wall, the wall having an outer surface, an outer surface circumference, and an outer surface length measured longitudinally, wherein a first line extends longitudinally along the outer surface, wherein a second line extends longitudinally along the outer surface, and wherein the second line is circumferentially offset from the first line by 180 degrees;
a plurality of first slots through the cylindrical wall and sequentially present along the first line, wherein each first slot has a first slot length measured circumferentially on the outer surface between first slot ends, wherein each first slot has a first slot width measured longitudinally on the outer surface, and wherein the first slot length is greater than the first slot width;
a plurality of first arches, wherein each first arch is present between a pair of longitudinally-adjacent first slots of the plurality of first slots, wherein each first arch has a first arch length measured circumferentially on the outer surface, wherein each first arch has a first arch width measured longitudinally on the outer surface, and wherein the first arch length is greater than the first arch width;
a plurality of second slots through the cylindrical wall and sequentially present along the second line, wherein each second slot has a second slot length measured circumferentially on the outer surface between second slot ends, wherein each second slot has a second slot width measured longitudinally on the outer surface, and wherein the second slot length is greater than the second slot width;
a plurality of second arches, wherein each second arch is present between a pair of longitudinally-adjacent second slots of the plurality of second slots, wherein each second arch has a second arch length measured circumferentially on the outer surface, wherein each second arch has a second arch width measured longitudinally on the outer surface, and wherein the second arch length is greater than the second arch width;

a plurality of bridges connecting the first arches to the second arches, wherein the plurality of bridges defines a first serpentine backbone and a second serpentine backbone; and an expansion gap including a third slot extending through the cylindrical wall, the expansion gap dividing one of the serpentine backbones, wherein the third slot has a third slot length measured circumferentially on the outer surface, wherein the third slot length is greater than the first slot length of the plurality of first slots and the second slot length of the plurality of second slots;

wherein at least one of the first slot length and the second slot length is greater than one-half of the outer surface circumference;

an outer body surrounding the curve shape strut; and an insert component surrounded by the curve shape strut.

* * * * *